United States Patent
Vogl (10) Patent No.: US 9,423,350 B2
(45) Date of Patent: Aug. 23, 2016

(54) METHOD AND DEVICE FOR DETERMINING A CONCENTRATION

(71) Applicant: VWM GMBH, Zwerndorf (AT)

(72) Inventor: Wolfgang Vogl, Zwerndorf (AT)

(73) Assignee: VWM GMBH, Zwerndorf (Weiden A. D. March) (AT)

( * ) Notice: Subject to any disclaimer, the term of this patent is extended or adjusted under 35 U.S.C. 154(b) by 0 days.

(21) Appl. No.: 14/765,921

(22) PCT Filed: Feb. 10, 2014

(86) PCT No.: PCT/AT2014/050036
§ 371 (c)(1),
(2) Date: Aug. 5, 2015

(87) PCT Pub. No.: WO2014/124476
PCT Pub. Date: Aug. 21, 2014

(65) Prior Publication Data
US 2015/0362430 A1    Dec. 17, 2015

(30) Foreign Application Priority Data

Feb. 15, 2013 (AT) .............................. A 50110/2013

(51) Int. Cl.
*G01J 1/58*    (2006.01)
*G01N 21/64*   (2006.01)
*G01N 21/27*   (2006.01)

(52) U.S. Cl.
CPC .............. *G01N 21/64* (2013.01); *G01N 21/274* (2013.01); *G01N 2021/6491* (2013.01); *G01N 2201/061* (2013.01)

(58) Field of Classification Search
CPC ........................... G01N 21/64; G01N 2201/61
USPC ...................................................... 250/459.1
See application file for complete search history.

(56) References Cited

U.S. PATENT DOCUMENTS

| 4,162,851 A | 7/1979 | Wada |
| 2009/0006004 A1 | 1/2009 | Sens et al. |

(Continued)

FOREIGN PATENT DOCUMENTS

| DE | 102005062910 | 7/2007 |
| DE | 102009020252 | 11/2010 |

(Continued)

OTHER PUBLICATIONS

International Search Report for corresponding international application PCT/AT2014/050036 mailed May 20, 2014.

(Continued)

*Primary Examiner* — David Porta
*Assistant Examiner* — Meenakshi Sahu
(74) *Attorney, Agent, or Firm* — Nevrivy Patent Law Group P.L.L.C.

(57) ABSTRACT

The invention relates to a method and a device (1) for determining a concentration (c) of a fluorescent substance in a medium, wherein an excitation radiation having an excitation wavelength ($\lambda_{ex}$) is radiated through the medium having the fluorescent substance so that the fluorescent substance is excited in such a way that the fluorescent substance emits a fluorescence radiation having a fluorescence wavelength ($\lambda_{em}$), wherein the intensity of the fluorescence ($I_{fluor}$) is measured, from which the concentration (c) of the fluorescent substance in the medium is determined, wherein additionally the intensity ($I_{trans,ex}$) of a transmitted portion of the excitation radiation is measured, wherein the concentration (c) of the fluorescent substance is determined from the intensity of the transmitted portion of the excitation radiation ($I_{trans,ex}$) and the intensity of the fluorescence ($I_{fluor}$).

14 Claims, 6 Drawing Sheets

(56) References Cited

U.S. PATENT DOCUMENTS

| | | | |
|---|---|---|---|
| 2010/0282982 A1* | 11/2010 | Schreiber | G01N 21/6486 250/459.1 |
| 2012/0228519 A1 | 9/2012 | Gilmore et al. | |

FOREIGN PATENT DOCUMENTS

| | | |
|---|---|---|
| JP | S6394136 A | 4/1988 |
| WO | 93/07472 | 4/1993 |
| WO | 2009/079629 | 6/2009 |

OTHER PUBLICATIONS

English Abstract of S6394136 dated Apr. 25, 1988.
Written Opinion of the International Search Authority for corresponding international application PCT/AT2014/050036 mailed Aug. 15, 2014.
English Translation of the written opinion of the International Searching Authority for corresponding international application PCT/AT2014/050036 mailed Aug. 15, 2014.

* cited by examiner

METHOD AND DEVICE FOR DETERMINING A CONCENTRATION

The invention relates to a method for determining a concentration of a fluorescent substance in a medium, wherein an excitation radiation having an excitation wavelength is radiated through the medium having the fluorescent substance so that the fluorescent substance is excited in such a way that the fluorescent substance emits a fluorescence radiation having a fluorescence wavelength, wherein the intensity of the fluorescence radiation is measured, from which the concentration of the fluorescent substance in the medium is determined.

Furthermore, the invention relates to a device for determining a concentration of a fluorescent substance in a medium, including at least a first radiation source for emitting an excitation radiation having an excitation wavelength, a first sensor for measuring the intensity of a fluorescence radiation being excited by the excitation radiation and having a fluorescence wavelength, and a computing unit for determining the concentration of the fluorescent substance depending on the intensity of the fluorescence radiation.

A method for determining the presence of a fluorescent substance in a medium is known from the prior art, in which the fluorescent substance is specifically excited for emitting a fluorescence radiation via an excitation radiation. The intensity of the fluorescence radiation is measured in order to derive the presence of the fluorescent substance depending on the measuring result. In general, however, the measuring of fluorescence as such is not considered a reliable quantitative measuring method since the concentration of the fluorescent substance can only be derived from the intensity of the fluorescence radiation in few cases. In immunology, for example, antibodies are provided with a fluorescent chemical group so the sites binding the antibodies may be recognised by means of fluorescence. A partial quantitative determination of the concentration of antigens is also possible in this way.

In any case, observations in practice revealed that the desired accuracy in the determination of the concentration by measuring fluorescence is usually not obtained. For example, it has been observed that the geometry of the measuring chamber has an impact on the accuracy of the measuring. Under varying temporal conditions, satisfactory results could not be obtained by the known method, either. This problem has not been solved as of yet.

Accordingly, the object of the present invention is to create a method and a device of the initially mentioned type for allowing a highly accurate determination of the concentration of a fluorescent substance. In particular, the impact of the geometry of the measuring chamber on the accuracy of the measuring should be reduced and/or eliminated. Moreover, the determination of the concentration should be carried out accurately even under varying temporal conditions.

For achieving this object according to the invention, the intensity of a transmitted portion of the excitation radiation is measured as well, with the concentration of the fluorescent substance being determined from the intensity of the transmitted portion of the excitation radiation and the intensity of the fluorescence radiation.

Advantageously, not only fluorescence is measured, as has previously been the case, but it is also taken into account that the absorption of the excitation light in the sample having the fluorescent substance may also have an impact on the intensity of the measured fluorescence radiation. The strength of the impact of the absorption on the determination of the concentration may be particularly dependent on the distances the light travels within the sample. According to this, the impact of the absorption depends mainly on the geometry of the measuring chamber. Since these effects have not been taken into account in previously used methods for measuring fluorescence, the concentration of the fluorescent substance in the sample could not be derived from the measured intensity of fluorescence as such. In contrast, the method according to the invention may be used as a highly accurate quantitative method for determining the concentration of the fluorescent substance. It has been observed that absorption increases proportionally to fluorescence in the method for determining the concentration of the fluorescent substance. This means that the further the excitation light required for measuring fluorescence penetrates the sample medium, the more it is diminished, so the resulting fluorescence signal is attenuated. Moreover, in practice, an absorption of the excitation light in the sample, with no causal connection to the fluorescence or the concentration of the substance causing the fluorescence, occurs frequently in unknown samples. As a consequence, measuring fluorescence alone encompasses an error inherent in the system, which cannot be corrected by information from the measuring of fluorescence. According to the invention, this error is eliminated by measuring the transmitted portion of the excitation radiation, which gives information about the absorption of the excitation radiation when it passes through the measuring volume. The concentration of the fluorescent substance is then determined based on both the fluorescence and the transmission of the excitation radiation. This method is particularly advantageous if a blurring of the sample and/or an increased absorption of the excitation radiation due to other reasons, for example due to adding a reaction chemistry, leads to a diminishing of the excitation radiation penetrating the medium and subsequently to an attenuated fluorescence signal. When measuring fluorescence alone, the change in the signal could not be distinguished from lower fluorescence, so an inaccurate and/or incorrect result in determining the concentration were obtained. In contrast to this, the concurrent measuring of absorption and fluorescence has the advantage that the transmitted portion of the excitation radiation may be used for correcting non-linearities and incorrect measuring due to the absorption of the excitation radiation in the sample. This is advantageous, for example, if different geometries of the measuring chambers receiving the sample need to be taken into account. Furthermore, after adding a reaction chemistry, in particular a substrate, a statement about the qualitative state of the reaction chemistry added may be made from the relation between absorption and fluorescence. Another advantage of the invention is that in a longer measuring process, changes in the concentration may be distinguished from variations in the permeability of the sample with high accuracy. Here, it is particularly preferred for the intensity of the fluorescence and the intensity of the transmission of the excitation radiation to be measured simultaneously at the same volume element of the medium having the fluorescent substance. This is particularly advantageous if the sample is inhomogeneous or its state is changing rapidly in terms of time. With stable and homogeneous samples, which are present in sufficient amounts as well, however, fluorescence and transmission of the excitation radiation may alternatively be measured one after another in the same device or in separate measuring devices (at the same time as well).

According to a particularly preferred embodiment a fluorescence absorption radiation having the fluorescence wavelength is radiated through the medium having the fluorescent substance, the intensity of a transmitted portion of the fluorescence absorption radiation is measured, and the concentration of the fluorescent substance is determined from the intensity of the transmitted portion of the excitation radiation, the intensity of the fluorescence radiation and the intensity of the transmitted portion of the fluorescence absorption radiation. In this embodiment, the transmission and/or absorption of the sample when the fluorescence wavelength passes through it is thus used as a further input parameter for determining the concentration of the fluorescent substance. Here, measuring the transmitted portion of the fluorescence absorption radiation is done with the excitation radiation being switched off, so the transmission of the sample when the fluorescence wavelength passes through it may be determined independently from the fluorescence excited by the excitation radiation. Accordingly, in this embodiment, the concentration of the fluorescent substance is determined from a triplet of measured values which is composed of both the fluorescence radiation and the transmission of the excitation radiation and the fluorescence absorption radiation. Here, the transmission of the excitation radiation and/or the fluorescence absorption radiation when passing through the medium having the fluorescent substance are added to the fluorescence signal as corrective values.

In order to obtain even more accurate measuring results, preferably the intensity of a scattered light having the excitation wavelength is measured as well, and the concentration of the fluorescent substance is determined from the intensity of the transmitted portion of the excitation radiation, the intensity of the fluorescence radiation and the intensity of the scattered light and, if applicable (i. e. if measured), also the intensity of the transmitted portion of the fluorescence absorption radiation. Measuring the scattered radiation is in particular done by a third radiation sensor, which is preferably sensitive for the excitation wavelength and/or upstream of which an appropriate band pass filter having a central wavelength $\lambda_{ex}$ is arranged.

For a highly accurate measuring of the concentration, preferably the concentration of the fluorescent substance is determined from a set of characteristic curves, which indicates the concentration of the fluorescent substance depending on the intensity of the transmitted portion of the excitation radiation, the intensity of the fluorescence radiation and, if applicable (i. e. if measured), the intensity of the transmitted portion of the fluorescence absorption radiation and/or the intensity of the scattered light. The set of characteristic curves may be obtained empirically. Alternatively, a computing model relating the input parameters for determining the concentration of the fluorescent substance to one another may be used.

Moreover, it is favourable for certain applications if the set of characteristic curves indicates the concentration of the fluorescent substance depending on the pH and/or the temperature of the medium as well, thus obtaining a set of characteristic curves of a correspondingly higher number of dimensions.

Here, it is particularly favourable if the set of characteristic curves is determined by a measuring method carried out before the determination of the concentration of the fluorescent substance, in which the intensity of the fluorescence radiation, the intensity of the transmitted portion of the excitation radiation and, if applicable, the intensity of the transmitted portion of the fluorescence absorption radiation and/or the intensity of the scattered light are measured for each of a number of given calibration concentrations of the fluorescent substance. Advantageously, this makes it possible to determine an unambiguous relation between the concentration of the fluorescent substance and the input parameters, specific to the measuring set-up, which is used for the determination of an unknown concentration of the fluorescent substance. For improving the resolution it is favourable if the measuring points of the set of characteristic curves are interpolated by an approximation curve in a manner known per se. If taking into account the scattered light, several measuring runs for the same absorption and varying scattering may be carried out. As an alternative for such a measuring and/or calibration method, the relation between the concentration and the individual measuring parameters may also be obtained via a mathematical connection.

In order to improve the accuracy of the measuring, it is favourable if the transmitted portion of the excitation radiation is redirected after passing through the medium having the fluorescent substance before measuring the intensity of the transmitted portion of the excitation radiation. In this way, interferences, which might occur when measuring the transmission of the excitation radiation in the direction of radiation passing through the medium having the fluorescent substance, may be avoided in an advantageous manner.

The device of the initially mentioned type is characterised in that a second sensor for measuring the intensity of a transmitted portion of the excitation radiation is provided, with the computing unit being set up for determining the concentration of the fluorescent substance depending on the intensity of the transmitted portion of the excitation radiation and the intensity of the fluorescence radiation.

The device provides the same advantages and technical effects as the previously discussed method, so reference is made to the above statements. Preferably, the computing unit has a memory in which a set of characteristic curves is stored, including the relations between the concentration of the fluorescent substance and the intensity of the transmitted portion of the excitation radiation, the intensity of the fluorescence radiation, and preferably also the intensity of the transmitted portion of the fluorescence absorption radiation.

In order to further improve the accuracy of the determination of the concentration, it is favourable if a second radiation source is provided for passing a fluorescence absorption radiation having the fluorescence wavelength through the medium having the fluorescent substance. The second radiation source may be switched on and/or off independently from the first radiation source, so the intensity of the transmitted portion of the fluorescence absorption radiation, i. e. the absorption of a radiation having the fluorescence wavelength when passing through the medium, may be determined in the on state of the second radiation source and in the off state of the first radiation source.

Preferably, the first sensor is set up for measuring the intensity of the transmitted portion of the fluorescence absorption radiation. Alternatively, a dedicated, third sensor may be provided for measuring the transmitted portion of the fluorescence absorption radiation. The first sensor is connected to the computing unit, which receives the intensity of the fluorescence and the intensity of the fluorescence absorption radiation as further input parameters (in addition to the transmission of the excitation radiation) for determining the concentration of the fluorescent substance.

Furthermore, it is preferred to provide a third sensor for measuring the intensity of a scattered light. The third sensor is connected to the computing unit, which receives the intensity of the scattered light as a further input parameter for determining the concentration of the fluorescent substance.

According to a preferred embodiment, a reference sensor for calibrating the first and the second radiation source, respectively, is associated to the first radiation source and/or the second radiation source. In a preferred embodiment, the reference sensor measures the intensity of the excitation radiation continuously, for example by a consistent percentage of the excitation light being coupled out of the light path of the excitation light and being passed to the reference sensor by means of a partially permeable mirror. This reference signal is compared to the measured (transmission and fluorescence) signals at any time. In this way, the measured signals are always related to the intensity of the excitation light measured by the reference sensor at the same time. This guarantees that possible fluctuations in the intensity of the excitation light will have no impact on the measuring result, in an advantageous manner.

In a preferred application, a measuring chamber, in particular a cuvette, is provided for receiving the medium having the fluorescent substance. Preferably, the medium having the fluorescent substance is present as a liquid sample. Alternatively, the concentration of a fluorescent substance may be determined in a gaseous medium. In some embodiments it is favourable if multiple measuring chambers are provided, each being adapted for a different fluorescence and/or excitation wavelength, so the concentrations of different fluorescent substances may be determined using the same device. Here, it is favourable to use sets of characteristic curves adapted to the respective wavelengths, preferably by means of the measuring method described above.

According to a further preferred embodiment the first radiation source should be set up for emitting an excitation radiation having multiple excitation wavelengths, in particular having a substantially continuous excitation spectrum. Preferably, sets of characteristic curves of the concentration for an at least substantially continuous wavelength range of the excitation and/or fluorescence wavelength are used for this, so the method may be expanded to the determination of the concentration of fluorescent substances in an at least substantially continuous wavelength range. For this purpose, the measuring method described above may be carried out in narrow frequency spacings for a variety of excitation and/or fluorescence wavelengths, so the sets of characteristic curves for the wavelength range of interest are obtained. In this case, it is not required for the first radiation source to be set up for emitting a monochromatic excitation radiation (or the second radiation source to be set up for emitting a monochromatic fluorescence absorption radiation) as is preferred when examining a single, substantially discrete fluorescence and/or excitation wavelength. Instead, the first radiation source is set up for emitting an excitation radiation having multiple excitation wavelengths, in particular having a substantially continuous excitation spectrum. The first or the second sensor and, if applicable, the reference sensor are each preferably provided as spectrometers in this embodiment. Moreover, it is favourable in this embodiment if both the second radiation source for emitting the fluorescence absorption radiation and, if applicable, the sensor for the intensity of the scattered light, are omitted since the information to be represented thereby are already included in the absorption and/or fluorescence spectrum.

In order to avoid interferences compromising the measuring accuracy it is favourable if a deflecting mirror for deflecting the transmitted portion of the excitation radiation is arranged between the measuring chamber and the second sensor.

Preferably, the deflecting mirror effects a deflection of the transmitted portion of the excitation radiation by substantially 90°. Advantageously, this may significantly improve accuracy when measuring the transmission of the excitation radiation.

For coupling out the excitation radiation it is particularly favourable if a beam splitter, in particular a frequency-selective beam splitter, is provided as the deflecting mirror. Preferably, the frequency-selective beam splitter is designed as a long pass (i. e. as a low pass in the frequency space), which does not reflect radiation having the fluorescence wavelength but lets it pass. In particular, this embodiment may make it possible that radiation having the fluorescence wavelength and being reflected by the second sensor does not get back through the measuring chamber and, subsequently, to the first sensor. At the same time this may prevent radiation having the fluorescence wavelength from moving from the measuring chamber to the second sensor. This is particularly important because the intensities of transmitted radiation and fluorescence radiation may be different by several orders of magnitude. The first sensor (fluorescence sensor) may thus be substantially more sensitive than the second sensor (transmission sensor). Preferably, the second radiation source for emitting the fluorescence absorption radiation is also associated to the deflecting mirror. Also, it is favourable here if the beam splitter is frequency-selective. Preferably, the threshold wavelength of the frequency-selective beam splitter is between the excitation wavelength and the fluorescence wavelength. This makes it possible, in particular, for the transmitted portion of the excitation radiation to get into the second sensor substantially in its entirety.

The invention will be discussed in further detail by means of preferred exemplary embodiments illustrated in the drawings, but without being limited to them, below. In the drawings.

Figure 1:
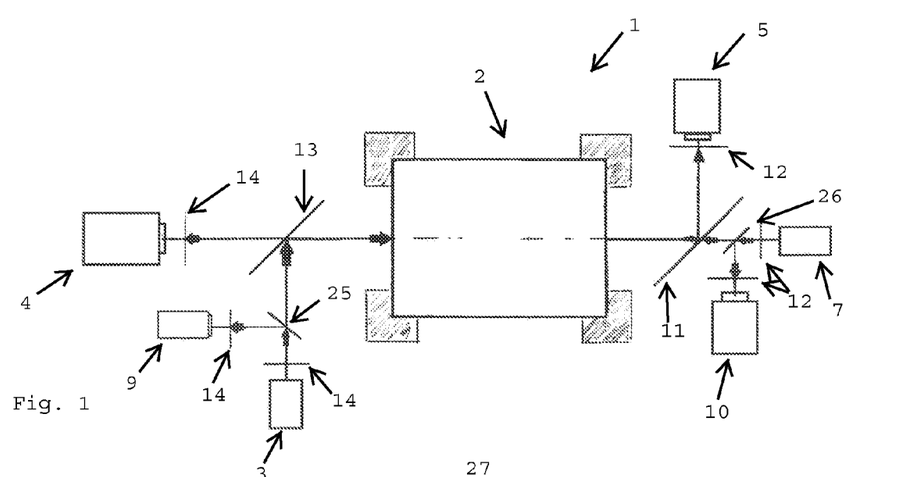
FIG. 1 is a view of a device according to the invention for determining a concentration of a fluorescent substance in a medium.

FIG. 1 shows a device 1 for determining a concentration c of a fluorescent substance in a medium received in a measuring chamber 2. In the embodiment shown, a cuvette is provided as the measuring chamber 2, in which a liquid sample having the fluorescent substance is received. The device 1 includes a first radiation source 3 for emitting an excitation radiation having an excitation wavelength $\lambda_{ex}$. In addition, a first sensor 4 is provided for measuring the intensity $I_{fluor}$ of a fluorescence radiation excited by the excitation radiation (in short: fluorescence) having a larger fluorescence wavelength $\lambda_{em}$ compared to the excitation wavelength $\lambda_{ex}$. As is known in general, the fluorescence light always has a larger wavelength, i. e. a lower frequency (and/or energy), than its excitation light.

As can further be seen in FIG. 1, a second sensor 5 is also provided for measuring the intensity of a transmitted portion of the excitation radiation $I_{trans,ex}$ (in short: transmission of the excitation radiation). The transmission of the excitation radiation, which is indirectly proportional to the absorption of the excitation radiation when passing through the sample, is measured at the same time as the intensity of the fluorescence radiation $I_{fluor}$.

Moreover, a computing unit 6 (cf. FIG. 5) is provided for determining the concentration c of the fluorescent substance. In the embodiment shown, the concentration c is determined not only dependent on the fluorescence but also dependent on the transmission of the excitation radiation. Thereby, the accuracy of the measuring of the concentration may be increased significantly with respect to conventional methods, in which the fluorescence signal alone is considered, provided the measuring of the fluorescence as such is able to allow a quantitative determination of the concentration in the first place.

As can further be seen in FIG. 1, a second radiation source 7 is also provided for passing a radiation having the fluorescence wavelength, hereinafter referred to as fluorescence absorption radiation, through the sample. The intensity $I_{trans,em}$ of the transmitted portion (in short: transmission) of the fluorescence absorption radiation is measured by means of the first sensor 3 while the first radiation source 3 is switched off.

As can further be seen in FIG. 1, a reference sensor 9 is associated to the first radiation source 3 and a reference sensor 10 is associated to the second radiation source 7, allowing the calibration of the first 3 and the second radiation source 7, respectively. For this, a consistent, comparably low percentage of the excitation light is coupled out of the light path of the excitation light and passed to the reference sensor 9 by means of a partially permeable mirror 25 in order to continuously capture the intensity of the excitation radiation. The transmission of the excitation radiation and the fluorescence (and, if applicable, the intensity of scattered light as well, cf. FIG. 3) is referred to the reference signal at any time for performing a calibration of the measuring signals. Accordingly, a second partially permeable mirror 26 for redirecting a (comparably small) portion of the fluorescence absorption radiation into the reference sensor 10 is provided for the second radiation source 7. This makes it possible to perform a calibration with regard to the fluorescence absorption radiation.

As can further be seen in FIG. 1, the device 1 in the embodiment shown also has a deflecting mirror 11, which is arranged between the measuring chamber 2 and the second sensor 5. Thereby, the transmitted portion of the excitation radiation is deflected relative to the direction of passing through after leaving the measuring chamber 2. In doing so, the deflecting mirror 11 causes a deflection of the transmitted portion of the excitation radiation by substantially 90° relative to the direction of the excitation radiation when passing through the measuring chamber 2. In the embodiment shown, a beam splitter is provided as the deflecting mirror 11, which is formed frequency-selective having a threshold wavelength between the excitation and the fluorescence wavelength, so radiation having the fluorescence wavelength is not reflected but allowed to pass through. This prevents both radiation having the fluorescence wavelength and being reflected by the second sensor 5 from getting through the measuring chamber to the first sensor 4 and radiation having the fluorescence wavelength from getting from the measuring chamber 2 to the second sensor 5.

In the embodiment shown, an (optional) band pass filter 12 is arranged upstream of each of the reference sensor 10, the second radiation source 7 and the second sensor 5. At the reference sensor 10, a reference value for the intensity of the fluorescence absorption radiation is obtained in order to be able to take into account possible fluctuations in the intensity of the fluorescence absorption radiation.

As can further be seen in FIG. 1, a further deflecting mirror 13 for coupling the excitation radiation into the measuring chamber 2 by deflecting it by substantially 90° is provided between the first radiation source 3 and the measuring chamber 2. According to the deflecting mirror 11, the deflecting mirror 13 is designed as a frequency-selective beam splitter having a threshold wavelength between the excitation wavelength $\lambda_{ex}$ and the fluorescence wavelength $\lambda_{em}$. The first sensor 4 is disposed parallel to the direction of passing through the measuring chamber 2, on the side of the deflecting mirror 13 facing away from the measuring chamber 2. Moreover, an optional band pass filter 14 is arranged upstream of each of the first sensor 4, the reference sensor 9 and the first radiation source 3. The optional use of the band pass filters 12, 14 may in particular depend on the characteristics of the sensors or the radiation sources.

Figure 2:
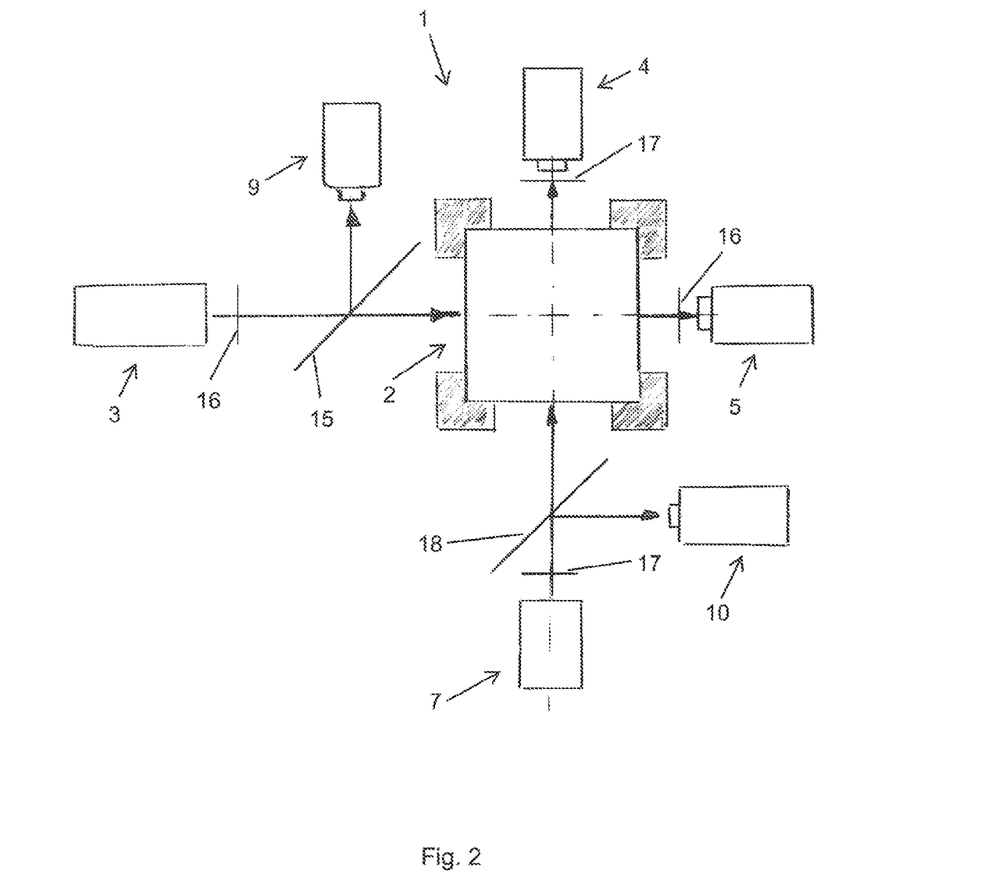
FIG. 2 is a view of an alternative embodiment of the device for determining the concentration of the fluorescent substance.

FIG. 2 shows an alternative embodiment of the device 1 for determining the concentration c of the fluorescent substance, with only the differences to FIG. 1 being discussed below.

According to FIG. 2, a partially permeable mirror 15 for coupling a portion of the excitation radiation into the measuring chamber 2 and/or passing it to the reference sensor 9 is arranged between the first radiation source 3 and the measuring chamber 2. At the reference sensor 9, a reference signal for the intensity of the excitation radiation is continuously captured. Optionally, a filter 16 adapted to the excitation wavelength may be arranged upstream of the first radiating source 3. A further filter 16 for the excitation wavelength $\lambda_{ex}$ is arranged upstream of the second sensor 5 for capturing the transmission of the excitation radiation. Like filters 17, however adapted to the fluorescence wavelength $\lambda_{em}$, are associated to the second radiation source 7 for emitting the fluorescence absorption radiation and the first sensor 4 for capturing the transmission of the fluorescence absorption radiation and/or the fluorescence.

According to FIG. 2, a further partially permeable mirror 18 for coupling a portion of the fluorescence absorption radiation into the measuring chamber 2 and/or passing it to the reference sensor 10 is arranged between the second radiation source 7 and the measuring chamber 2. At the reference sensor 10, a reference signal for the intensity of the fluorescence absorption radiation is continuously captured, allowing the exact determination of the transmission of the fluorescence absorption radiation (and the absorption of the fluorescence radiation in the sample from it).

According to FIG. 2, the fluorescence is measured in an angle of in particular 90° to the radiation direction of the excitation radiation. In contrast to FIG. 1, no beam splitters are provided in the light path between the measuring chamber 2 and the first sensor 4 and/or in the light path between the measuring chamber 2 and the second sensor 5.

Figure 3:
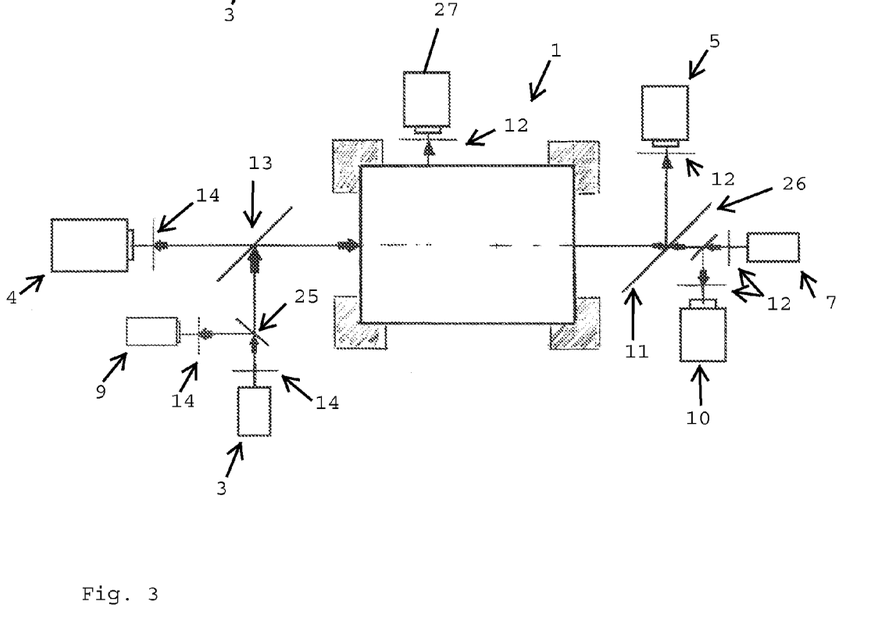
FIG. 3 is a view of a further embodiment of the device for determining the concentration of the fluorescent substance.

As can be seen in FIG. 3, in this embodiment, the intensity $I_{streu,ex}$ of a scattered radiation having the excitation wavelength $\lambda_{ex}$ is also measured by means of a third sensor 27 and used for determining the concentration of the fluorescent substance. A band pass filter 12 is (optionally) arranged upstream of the third sensor 27. Otherwise, the arrangement according to FIG. 3 is identical to the embodiment shown in FIG. 1 while a third sensor 27 for capturing the intensity of the scattered light may, of course, be provided in the embodiment according to FIG. 2 as well.

Figure 4:
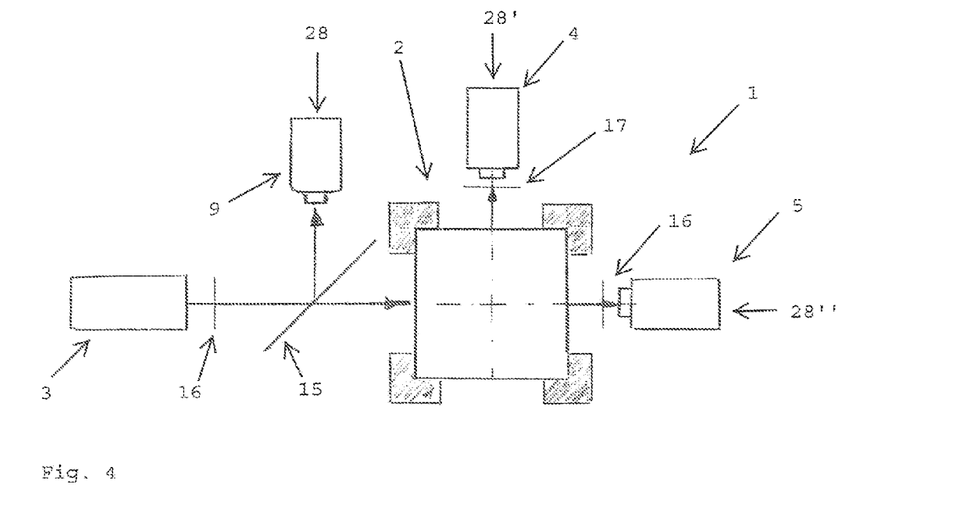
FIG. 4 is a view of a further embodiment of the device for determining the concentration of the fluorescent substance.

According to FIG. 4, a first radiation source 3 having a wide, continuous excitation spectrum is used. Here, the first sensor 4, the second sensor 5 and the reference sensor 9 are designed as spectrometers 28, 28', 28". In this embodiment, the second radiation source 7 for emitting the fluorescence absorption radiation and the third sensor 27 for the intensity of the scattered light may be omitted.

Figure 5:
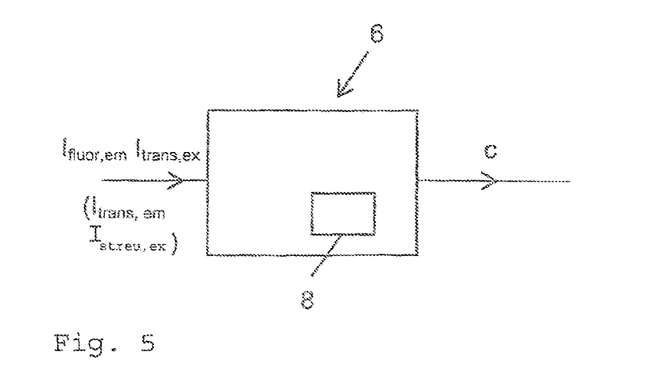
FIG. 5 is a schematic view of a computing unit for determining the concentration of the fluorescent substance.

As can be seen in FIG. 5, the computing unit 6 has the fluorescence, the transmission of the excitation radiation and, optionally, either or both of the transmission of the fluorescence absorption radiation and the intensity of the scattered light as input parameters. The computing unit 6 includes a memory 8 in which a set of characteristic curves for determining the concentration c of the fluorescent substance from the input parameters is stored. As the output parameter of the computing unit 6, the computing unit 6 gives the sought-after concentration c of the fluorescent substance.

As has already been mentioned, the concentration of the fluorescent substance is determined by the computing unit 6 from the measuring parameters, which are linked by a set of characteristic curves stored in the memory 8. The set of characteristic curves may be determined in a measuring method performed before the determination of the concentration, which is discussed below.

Figure 6:
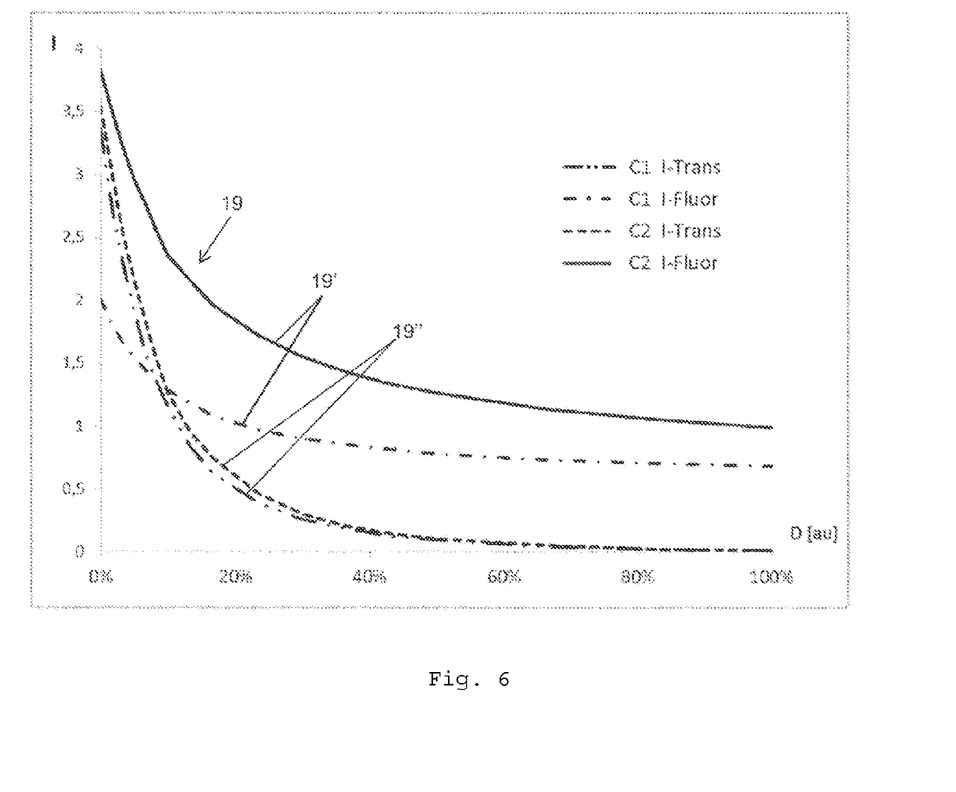
FIG. 6 is a diagram for illustrating the connection between the excited fluorescence and/or the transmission of the excitation radiation and the permeability of the medium, wherein different measuring curves for consistent calibration concentrations are illustrated.

According to FIG. 6, in a first step of the measuring and/or calibration method for defined concentrations c1, c2 of the fluorescent substance, individual measuring curves 19 are established, wherein both the fluorescence (measuring curves 19') and the transmission of the excitation radiation (measuring curves 19") are determined depending on a permeability D of the sample. The permeability D of the sample may be varied incrementally, for example, by adding an opaque substance. In this way, the measuring curves 19 for the fluorescence (measuring curves 19') and/or the transmission (measuring curves 19") are created depending on the permeability and/or opacity of the sample having consistent concentrations of the fluorescent substance.

Figure 7:
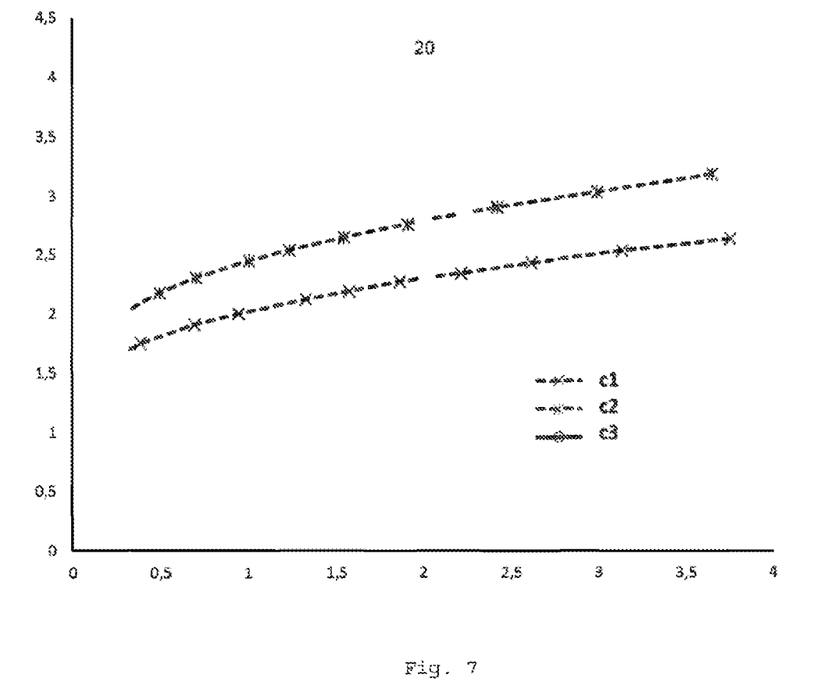
FIG. 7 is a diagram having a set of characteristic curves for determining the concentration of the fluorescent substance depending on the fluorescence and the transmission of the excitation radiation.

As can be seen in FIG. 7, the next step involves plotting the fluorescence against the transmission of the excitation radiation (measuring curves 20), wherein each measuring curve 20 represents a certain calibration concentration c1 to c3. In this way, a family of curves is created in two-dimensional space. Depending on the implementation, the transmission of the fluorescence absorption radiation or the intensity of the scattered light depending on the permeability of the sample may also be measured. In this case, in family of areas in three-dimensional space (not shown) is obtained instead of the two-dimensional diagram of FIG. 7. Each point in the diagram (two- or three-dimensional, depending on the implementation) represents a certain concentration of the fluorescent substance, so an unambiguous relation between the measuring parameters and the concentration c is obtained.

Alternatively, both scattered light and fluorescence absorption radiation may be taken into account, thus creating a four-dimensional matrix of state in which an unambiguous concentration c of the fluorescent substance is associated to any combination of the four parameters (i. e. fluorescence, transmission of the excitation radiation, transmission of the fluorescence absorption radiation and scattered radiation).

Depending on the number of the measuring curves 20, the accuracy of the determination of the concentration may be improved. Moreover, a mathematical and/or numerical interpolation may also be performed to allow a direct conversion of a doublet of measured values (and/or a triplet of measured values or a quartet of measured values, depending on the implementation) to the sought-after concentration c.

Figure 8:
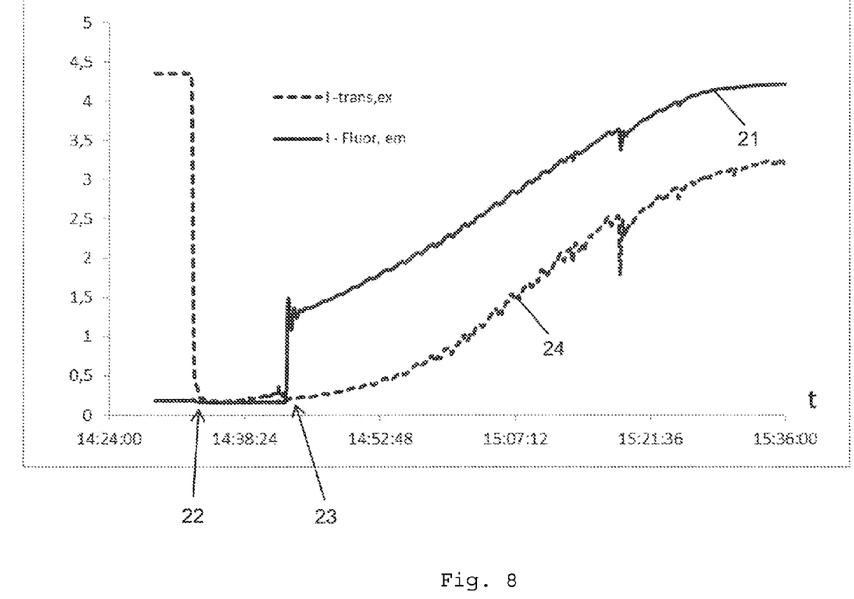
FIG. 8 is a diagram for illustrating an increase in the fluorescence signal, which cannot be attributed to an increase in the concentration of the fluorescent substance, but to an increase in the transmission of the excitation radiation.

The advantages of this method can be seen in an exemplary manner in FIG. 8, in which the temporal flow of fluorescence (signal 21) during a measuring process is illustrated schematically. The examination is performed on a liquid sample to which a buffer is added at a point in time 22. Later, a substrate is added, causing the formation of the fluorescent substance (arrow 23). After adding the substrate, the fluorescence signal starts to rise abruptly due to the inherent fluorescence of the substrate. Afterwards, a further temporal increase of the fluorescence may be observed, suggesting a rise in the concentration of the fluorescent substance. Measuring the transmission of the excitation radiation (signal 24), however, reveals that on introducing the buffer the transmission starts to drop abruptly since the buffer in the sample makes virtually no light reach the second sensor 5. Following this, the permeability of the sample increases again over time, so the transmission of the excitation radiation increases. Together with this, the intensity of the excitation signal for the fluorescence and, thus, the fluorescence signal increase as well. Accordingly, the supposed rise in fluorescence is not based on a change in the concentration of the fluorescent substance, but on an increase in the transmission of the excitation radiation.

The method described above may be used for determining the concentration of different types of fluorescent substances.

Here, the intensity of the fluorescence of a substance may depend on both the pH and the temperature at the time of measuring. The invention described allows to improve the accuracy of the fluorescence measuring even without a defined pH or without a defined temperature. In order to be able to determine the concentration of a substance in the sample, however, the sample measured should have the same pH and the same temperature as during calibration. This is guaranteed by adding a defined amount of a buffer and exact temperature control of the measuring equipment. Alternatively, the set of characteristic curves may be expanded to include the parameters pH and/or temperature, thus obtaining a set of characteristic curves having a correspondingly higher number of dimensions. Such a set of characteristic curves has four dimensions (when taking into account exclusively the intensity of the transmitted portion of the excitation radiation $I_{trans,ex}$ and the intensity of the fluorescence radiation $I_{fluor}$) or five or six dimensions (when taking into account the intensity of the transmitted portion of the fluorescence absorption radiation $I_{trans,em}$ and/or the intensity of the scattered light $I_{streu,ex}$ as well).

As an example for the method described above, determining the concentration of sodium fluorescein in bodies of water is described below.

Sodium fluorescein is used as a fluorescence tracer for examining groundwater streams. The ideal excitation wavelength for sodium fluorescein is 491 nm; the maximum fluorescence radiation is 516 nm. For determining the concentration of fluorescein in the sample, first, the measuring equipment is calibrated by establishing a set of characteristic curves as has been described above. For this, reference solutions are gauged one after another, each having a defined concentration of fluorescein and a consistent pH set by a buffer solution, for example pH 7. These reference solutions are gauged at a consistent temperature, for example at 25° C. In the course of calibration, each reference solution is measured repeatedly while successively adding increasing concentrations of an opaque substance such as formazine. The respective combinations of the measured values for intensity of fluorescence, intensity of transmission, and, if applicable, also for intensity of scattered light and intensity of fluorescence absorption radiation at consistent concentration of fluorescein and concurrently increasing concentration of formazine are recorded. This process is repeated for different concentrations of fluorescein in order to obtain a sufficiently dense set of characteristic curves, allowing to sufficiently plot the entire range of concentrations to be covered by interpolation or mathematical calculation.

After completing calibration, the measuring equipment is ready to use. Now, any sample, provided with a defined amount of buffer for setting the pH, is passed into the measuring equipment for determining the values of intensity for fluorescence, transmission and, if applicable, also scattered light and fluorescence absorption radiation. Using this set of measured data, the actual concentration of fluorescein is determined from the set of characteristic curves.

The invention claimed is:

1. A method for determining a concentration (c) of a fluorescent substance in a medium, wherein an excitation radiation having an excitation wavelength ($\lambda_{ex}$) is radiated through the medium having the fluorescent substance so that the fluorescent substance is excited in such a way that the fluorescent substance emits a fluorescence radiation having a fluorescence wavelength ($\lambda_{em}$), wherein the intensity of the fluorescence radiation ($I_{fluor}$) is measured, from which the concentration (c) of the fluorescent substance in the medium is determined, characterised in that additionally the intensity ($I_{trans,ex}$) of a transmitted portion of the excitation radiation is measured, wherein the concentration (c) of the fluorescent substance is determined from the intensity of the transmitted portion of the excitation radiation ($I_{trans,ex}$) and the intensity of the fluorescence radiation ($I_{fluor}$);

wherein furthermore a fluorescence absorption radiation having the fluorescence wavelength ($\lambda_{em}$) is radiated through the medium having the fluorescent substance, the intensity of a transmitted portion of the fluorescence absorption radiation ($I_{trans,em}$) is measured, and the concentration (c) of the fluorescent substance is determined from the intensity of the transmitted portion of the excitation radiation ($I_{trans,ex}$), the intensity of the fluorescence radiation ($I_{fluor}$) and the intensity of the transmitted portion of the fluorescence absorption radiation ($I_{trans,em}$);

wherein the intensity of the fluorescence radiation ($I_{flour}$) and the intensity of a transmitted portion of the fluorescence absorption radiation ($I_{trans,em}$) are measured on the same sensor.

2. The method according to claim 1, characterised in that the intensity of a scattered light ($I_{streu,ex}$) having the excitation wavelength ($\lambda_{ex}$) is measured as well, and the concentration (c) of the fluorescent substance is determined from the intensity of the transmitted portion of the excitation radiation ($I_{trans,ex}$), the intensity of the fluorescence radiation ($I_{fluor}$) and the intensity of the scattered light ($I_{streu,ex}$) and, if applicable, also the intensity of the transmitted portion of the fluorescence absorption radiation ($I_{trans,em}$).

3. The method according to claim 1, characterised in that the concentration (c) of the fluorescent substance is determined from a set of characteristic curves, which indicates the concentration (c) of the fluorescent substance depending on the intensity of the transmitted portion of the excitation radiation ($I_{trans,ex}$), the intensity of the fluorescence radiation ($I_{fluor}$) and, if applicable, the intensity of the transmitted portion of the fluorescence absorption radiation ($I_{trans,em}$) and/or the intensity of the scattered light ($I_{streu,ex}$).

4. The method according to claim 3, characterised in that the set of characteristic curves indicates the concentration of the fluorescent substance (c) depending on the pH and/or the temperature of the medium as well.

5. The method according to claim 3, characterised in that the set of characteristic curves is determined by a measuring method carried out before the determination of the concentration (c) of the fluorescent substance, in which the intensity of the fluorescence radiation ($I_{flour}$), the intensity of the transmitted portion of the excitation radiation ($I_{trans,ex}$) and, if applicable, the intensity of the transmitted portion of the fluorescence absorption radiation ($I_{trans,em}$) and/or the intensity of the scattered light ($I_{streu,ex}$) are measured for each of a number of given calibration concentrations (c1-c3) of the fluorescent substance.

6. The method according to claim 1, characterised in that the transmitted portion of the excitation radiation is redirected after passing through the medium having the fluorescent substance before measuring the intensity of the transmitted portion of the excitation radiation ($I_{trans,ex}$).

7. A device (1) for determining a concentration (c) of a fluorescent substance in a medium, including at least a first radiation source (3) for emitting an excitation radiation having an excitation wavelength ($\lambda_{ex}$), a first sensor (4) for measuring the intensity of a fluorescence radiation being excited by the excitation radiation and having a fluorescence wavelength ($\lambda_{em}$), and a computing unit (6) for determining the concentration of the fluorescent substance from the intensity of the fluorescence radiation, wherein a second sensor (5) for measuring the intensity of a transmitted portion of the excitation radiation is provided, with the computing unit (6) being set up for determining the concentration (c) of the fluorescent substance depending on the intensity of the transmitted portion of the excitation radiation ($I_{trans,ex}$) and the intensity of the fluorescence radiation ($I_{fluor}$);

wherein a second radiation source (7) is provided for passing a fluorescence absorption radiation having the fluorescence wavelength ($\lambda_{em}$) through the medium having the fluorescent substance; and wherein the first sensor (4) is also set up for measuring the intensity of the transmitted portion of the fluorescence absorption radiation ($I_{trans,em}$).

8. The device (1) according to claim 7, characterised in that a third sensor (27) is provided for measuring the intensity of a scattered light.

9. The device (1) according to claim 7, characterised in that a reference sensor (9, 10) for calibrating the first (3) and the second radiation source (7), respectively, is associated to the first radiation source (3) and/or the second radiation source (7).

10. The device (1) according to claim 7, characterised in that a measuring chamber (2), in particular a cuvette, is provided for receiving the medium having the fluorescent substance.

11. The device (1) according to claim 10, characterised in that a deflecting mirror (11) for deflecting the transmitted portion of the excitation radiation is arranged between the measuring chamber (2) and the second sensor (5).

12. The device (1) according to claim 11, characterised in that the deflecting mirror (11) effects a deflection of the transmitted portion of the excitation radiation by substantially 90°.

13. The device (1) according to claim 12, characterised in that a beam splitter, in particular a frequency-selective beam splitter, is provided as the deflecting mirror (11).

14. The device (1) according to claim 7, characterised in that the first radiation source (3) is set up for emitting an excitation radiation having multiple excitation wavelengths ($\lambda_{ex}$), in particular having a substantially continuous excitation spectrum, wherein the first sensor (4) and the second sensor (5) and, if applicable, the reference sensor (9) are each provided as spectrometers (28, 28', 28").

* * * * *